United States Patent [19]
Hauck et al.

[11] 3,963,724
[45] June 15, 1976

[54] INTERMEDIATES USEFUL IN THE PREPARATION OF ARYLDECAHYDROPYRROLO[3,4-f]QUINOLINES

[75] Inventors: Frederic Peter Hauck, Somerville; Joseph E. Sundeen, Trenton, both of N.J.

[73] Assignee: E. R. Squibb & Sons, Inc., Princeton, N.J.

[22] Filed: Feb. 13, 1975

[21] Appl. No.: 549,581

Related U.S. Application Data

[62] Division of Ser. No. 374,593, June 28, 1973, Pat. No. 3,891,652.

[52] U.S. Cl............................ 260/287 CF; 424/258
[51] Int. Cl.²............. C07D 491/04; C07D 471/04
[58] Field of Search............................. 260/287 CF

[56] References Cited
UNITED STATES PATENTS

3,081,306   3/1963   Lombardino ................ 260/287 CF

OTHER PUBLICATIONS

Wagner–Jauregg et al., "Helv. Chim. Acta", vol. 56, pp. 440–449.
Morrison et al., "Organic Chemistry," 1966, pp. 974–976.

*Primary Examiner*—Alton D. Rollins
*Assistant Examiner*—David E. Wheeler
*Attorney, Agent, or Firm*—Lawrence S. Levinson; Merle J. Smith; Stephen B. Davis

[57] ABSTRACT

Various intermediates useful in the preparation of 4-aryl-2,3,3a,4,5,6,7,8,9,9b-decahydro-1H-pyrrolo[3,4-f]quinolines are disclosed.

7 Claims, No Drawings

INTERMEDIATES USEFUL IN THE PREPARATION OF ARYLDECAHYDROPYRROLO[3,4-f]QUINOLINES

This is a division, of application Ser. No. 374,593, filed June 28, 1973, now U.S. Pat. No. 3,891,652.

This invention relates to blood pressure lowering agents, anti-inflammatory agents, antianginal and anti-arrhythmic agents of the following general formula

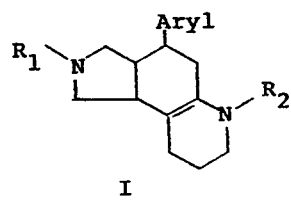

I wherein Aryl is selected from the group consisting of phenyl, naphthyl, and substituted phenyl or naphthyl, wherein said substituent is selected from the group consisting of lower alkyl, lower alkoxy, di(lower alkyl)amino, halogen and trifluoromethyl, and $R_1$ and $R_2$ are selected from the group consisting of hydrogen, lower alkyl, lower alkenyl, aryl, aryl-lower alkyl and aryl-lower alkenyl, and acid addition salts (Ia) thereof which have the formula

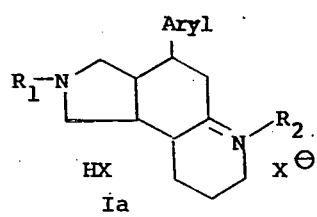

ia wherein Aryl, $R_1$ and $R_2$ are as previously described.

The preferred compounds of this invention are those wherein aryl is phenyl or p-methoxyphenyl and $R_1$ and $R_2$ are lower alkyl and the most preferred is the compound wherein aryl is p-methoxyphenyl and $R_1$ and $R_2$ are methyl.

In addition, this invention encompasses methods for preparing said compounds, the compositions containing said compounds and methods for using said compositions.

The term "lower alkyl" is intended to mean a straight or branched chain alkyl group of from one to eight carbon atoms.

The term "lower alkoxy" is intended to mean a straight or branched chain alkyl group of from one to eight carbon atoms linked directly to an oxygen atom.

The term "aryl" is intended to mean phenyl, naphthyl and substituted phenyl or naphthyl.

The term "substituted" when applied to aryl or phenyl is intended to encompass one or two substituents which may be alike or different and are selected from the following group: lower alkyl, lower alkoxy, halogen, trifluoromethyl, and di(lower alkyl)amino.

The term "acid addition salts" is intended to encompass the salts formed upon the addition of an acid to the compounds of this invention. Thus mono- or di- salts of this invention may be formed by the addition of such acids as hydrochloric acid, phosphoric acid, sulfuric acid, perchloric acid, acetic acid, citric acid, etc. The preferred acids are those which form pharmaceutically acceptable acid addition salts although other salts may be of use in purifying and storing the compounds of this invention. The salt form is best described by formula Ia.

The compounds of the present invention may exist in a number of isomeric forms such as steroisomeric forms, endo and exo forms, etc. All of these isomers are intended to be within the scope of the present invention.

The compounds of this invention are prepared from the readily available compounds of the formulae Aryl—CH=CHhalide

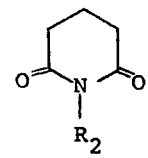

VI          VII

This invention also relates to the useful intermediates of the formulae:

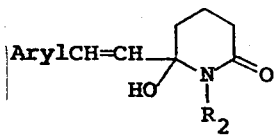

II

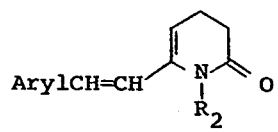

III

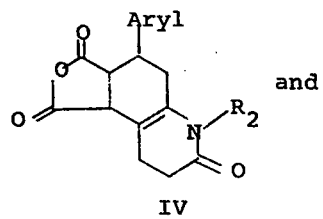

and

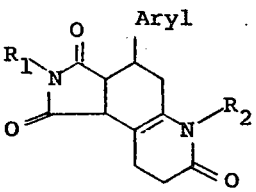

IV          V wherein Aryl and $R_2$ is as previously defined and halide is chlorine, bromine or iodine. Compound VI is converted to the Grignard reagent VIII, wherein Aryl—CH=CHMghalide

VII the preferred halide is the bromide, by reaction with magnesium turnings in an ethereal solvent, such as ether, tetrahydrofuran, dioxane, diglyme, etc. at from room temperature to about 100°C. for 15 minutes to about 24 hours. Compounds of the formula VIII are then added to compounds of the formula VII to give compounds of the formula II. Compounds of the formula II are generally converted to compounds of the formula III utilizing a dehydrating agent, such as p-toluene sulfonic acid or its monohydrate. Since compounds of the formula III tend to dimerize readily, the dehydration is usually carried out in the presence of a dienophile of the formula IX

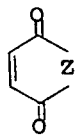

IX $R_1NH_2$

X wherein Z is —O— or

to give compounds of the formula IV or V. When compounds of the formula IX, wherein Z is —O—, are employed, compounds of the formula IV are obtained which are converted to compounds of the formula V by reaction with a compound of the formula X.

The dehydration reactions and Diels-Alder reactions are generally carried out from about 15° to about 80° in a lower alkyl anhydride solvent, such as acetic anhydride, for periods of from one hour to twenty four hours.

The compounds of formula V are converted into the compounds of this invention by a reduction reaction utilizing $LiAlH_4$ in an ethereal solvent, preferably tetrahydrofuran.

The compounds of formula I may be converted to their salts by reaction with acids, such as sulfuric acid, perchloric acid, hydrochloric acid, etc. The resultant compounds are best represented by formula XI

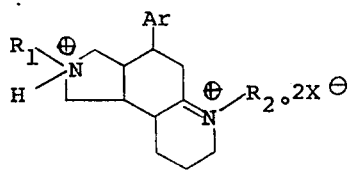

XI

The compounds of this invention and their non-toxic pharmaceutically acceptable salts have thus been found to be useful as antiinflammatory, antianginal and antiarrhythmic agents and to reduce blood pressure in mammals when administered in amounts ranging from about 2 mg. to about 25 mg. per kg. of body weight per day. A preferred dosage regimen for optimum results would be from about 10 mg. to about 20 mg. per kg. of body weight per day, and such dosage units are employed that a total of from about 500 mg. to about 1000 mg. of active ingredient for a subject of about 70 kg. body weight are administered in a 24 hours period.

The compounds of the present invention in the described dosages are intended to be administered orally; however, other routes such as rectally, intraperitoneally, subcutaneously, intramuscularly or intravenously may be employed.

The active compounds of the present invention are orally administered, for example, with an inert diluent or with an assimilable edible carrier, or they may be enclosed in hard or soft gelatin capsules, or they may be compressed into tablets, or they may be incorporated directly with the food of the diet. For oral therapeutic administration, the active compounds of this invention may be incorporated with excipients and used in the form of tablets, troches, capsules, elixirs, suspensions, syrups, wafers, chewing gum, and the like. Such compositions and preparations should contain at least 0.1% of active compound. The percentage in the compositions and preparations may, of course, be varied and may conveniently be between about 5% to about 75% or more of the weight of the unit. The amount of active compound in such therapeutically useful compositions or preparations is such that a suitable dosage will be obtained. Preferred compositions or preparations according to the present invention are prepared so that an oral dosage unit form contains between about 10 and 200 milligrams of active compound.

The tablets, troches, pills, capsules and the like may also contain the following: a binder such as gum tragacanth, acacia, corn starch or gelatin; and excipient such as dicalcium phosphate, a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain in addition to materials of the above type a liquid carrier such as a fatty oil. Various other materials may be present as coatings or to otherwise modify the physical form of the dosage unit, for instance, tablets, pills or capsules may be coated with shellac, sugar or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amounts employed.

The invention will be described in greater detail in conjunction with the following specific examples.

EXAMPLE 1

2,3,3a,4,5,7,8,9,9a,9b-Decahydro-2,6-dimethyl-4-phenyl-1H-pyrrolo[3,4-f]quinolinium chloride hydrochloride a. 1-methyl-2-styryl-2-hydroxy-6-piperidone The Grignard reagent prepared in 300 ml of THF from 24 g (1.0 mole) of magnesium and 42 g (0.30 mole) of β-bromostyrene is decanted from excess metal and added dropwise under nitrogen to a solution of 27 g (0.21 moles) of N-methyl glutarimide at 3°–5°. After 1 ½ hrs. at room temperature, the mixture is treated with 250 ml of saturated NH$_4$Cl solution with cooling. The separated aqueous layer is reextracted and the combined THF extracts washed with salt, dried over MgSO$_4$ and freed of solvent. Product is extracted into hot ether and crystallized on cooling to yield white crystals, mp 108°–112°C.

b. 1-methyl-7-phenyl-3,4,5,6,7,8-hexahydro-2-1H-quinolone-5,6-dicarboxylic acid anhydride A slurry of 0.8 g (2.6 mmole) of the above adduct in 12 ml of acetic anhydride is treated with 0.4 g (4.1 mmole) of maleic anhydride and 10 mg of toluenesulfonic acid hydrate. After standing overnight, the mixture is taken up in ether and seeded to yield the title compound as a crystalline solid, mp 201–204.

c. 2,3,3a,4,5,6,7,8,9,9b-Decahydro-2,6-dimethyl-4-phenyl-1H-pyrrolo[3,4-f]quinoline-1,3,7-trione The anhydride (0.55 g, 1.3 mmole) is taken up in 10 ml of 40% aqueous methylamine and the temperature raised slowly to 185° where it is held for 10 minutes in vacuo. Cooling leaves the title compound as a glass having an ir consistent with the product.

d. 2,3,3a,4,5,6,7,8,9,9b-Decahydro-2,6-dimethyl-4-phenyl-1H-pyrrolo[3,4-f]quinoline The above imide lactam (0.4 g, 1.0 mmole) in 20 ml of 1:1 ether: methylene chloride is treated with 0.5 g of lithium aluminum hydride in portions, then heated under reflux for 2 hrs. After decomposition with water, the mixture is filtered and the salts washed with methylene chloride. Evaporation gives 0.3 g of tacky yellow oil.

e. 2,3,3a,4,5,7,8,9,9a,9b-Decahydro-2,6-dimethyl-4-phenyl-1H-pyrrolo[3,4-f]quinolinium chloride hydrochloride The above product is dissolved in isopropanolether and treated with excess HCl. The crude salt is recrystallized from isopropanol-acetone-ether to yield a solid of mp 165°–175°.

Anal. Calcd. for C, 64.22; H, 7.94; N, 7.88; Cl, 19.35; Found C, 64.37; H, 8.24; N, 7.69; Cl, 20.19.

EXAMPLE 2

2,3,3a,4,5,7,8,9,9a,9b-Decahydro-2,6-dimethyl-4p-methoxyphenyl-1H-pyrrolo[3,4-f]quinolinium chloride hydrochloride Substituting p-methoxy-β-bromostyrene for β-bromostyrene in the procedure of Example 1a yields the corresponding substituted piperidone which is converted by the same sequence as Example 1 to the title compound.

EXAMPLE 3

2,3,3a,4,5,7,8,9,9a,9b-Decahydro-2,6-dimethyl-4-p-tolyl-1H-pyrrolo-[3,4-f]quinolinium chloride hydrochloride Substituting p-methyl-β-bromostyrene for β-bromostyrene in the procedure of Example 1 a yields the corresponding substituted piperidone which is converted by the same sequence as Example 1 to the title compound.

EXAMPLE 4

2,3,3a4,5,7,8,9,9a,9b-Decahydro-2,6-dimethyl-4-p-dimethylaminophenyl-1H-pyrrolo-[3,4-f]quinolinium chloride hydrochloride.

Substituting p-dimethylamino-β-bromostyrene for β-bromostyrene in the procedure of Example 1a yields the corresponding substituted piperidone which is converted by the same sequence as Example 1 to the title compound.

EXAMPLE 5

2,3,3a,4,5,7,8,9,9a,9b-Decahydro-2,6-dimethyl-4-p-fluorophenyl-1H-pyrrolo-[3,4-f]quinolinium chloride hydrochloride.

Substituting p-fluoro-β-bromostyrene for β-bromostyrene in the procedure of Example 1a yields the corresponding substituted piperidone which is converted by the same sequence as Example 1 to the title compound.

EXAMPLE 6

2,3,3a,4,5,7,8,9,9a,9b-Decahydro-6-ethyl-2-methyl-4-phenyl-1H-pyrrolo[3,4-f]quinolinium chloride hydrochloride.

Substituting N-ethyl glutarimide for N-methylglutarimide in the procedure of Example 1a yields the corresponding substituted piperidone which is converted by the same sequence as Example 1 to the title compound.

Example 7

6-Benzyl-2,3,3a,4,5,7,8,9,9a,9b-Decahydro-2-methyl-4-phenyl-1H-pyrrolo[3,4-f]quinolinium chloride hydrochloride.

Substituting N-benzylglutarimide for N-methylglutarimide in the procedure of Example 1a yields the corresponding piperidone which is converted by the same sequence as Example 1 to the title compound.

EXAMPLE 8

2-Benzyl-2,3,3a,4,5,7,8,9,9a,9b-Decahydro-6-methyl-4-phenyl-1H-pyrrolo[3,4-f]quinolinium chloride hydrochloride.

Substituting benzylamine for methylamine in the procedure of Example 1-c yields the corresponding imide lactam which is then reduced as in Example 1-d,e to the title compound.

EXAMPLE 9

2,3,3a,4,5,7,8,9,9a,9b-Decahydro-6-methyl-2,4-diphenyl-1H-pyrrolo[3,4-f]quinolinium chloride hydrochloride.

Substituting aniline for methylamine in the procedure of Example 1-c yields the corresponding imide lactam which is then reduced as in Example 1-d,e to the title compound.

EXAMPLE 10

2,3,3a,4,5,7,8,9,9a,9b-Decahydro-2-ethyl-6-methyl-4-phenyl-1H-pyrrolo[3,4-f]quinolinium chloride hydrochloride.

Substituting N-ethylmaleimide for maleic anhydride in the procedure of Example 1b and raising the reaction temperature to 60°–80° yields 2,3,3a,4,5,6,7,8,9,9b-decahydro-2-ethyl-6-methyl-4-phenyl-1H-pyrrolo[3,4-f]quinoline-1,3,7-trione directly which is then converted by the procedure of Example 1-d,e to the title compound.

What is claimed is:

1. A compound of the formula:

[structure shown with aryl, O, N-R₂, Z substituents]

wherein Z is $$-\overset{R_1}{\underset{|}{N}}-$$

or —O—; $R_1$ and $R_2$ are lower alkyl; and aryl is phenyl or p-methoxyphenyl.

2. The compound of claim 1 wherein Z is —O—.

3. The compound of claim 1 wherein Z is $$-\overset{R_1}{\underset{|}{N}}-.$$

4. The compound of claim 2 wherein aryl is phenyl and $R_2$ is methyl.

5. The compound of claim 2 wherein aryl is p-methoxyphenyl and $R_2$ is methyl.

6. The compound of claim 3 wherein aryl is phenyl and $R_1$ and $R_2$ are methyl.

7. The compound of claim 3 wherein aryl is p-methoxyphenyl and $R_1$ and $R_2$ are methyl.

* * * * *

UNITED STATES PATENT AND TRADEMARK OFFICE
CERTIFICATE OF CORRECTION

PATENT NO. : 3,963,724
DATED : June 15, 1976
INVENTOR(S) : Hauck et al.

It is certified that error appears in the above—identified patent and that said Letters Patent are hereby corrected as shown below:

Col. 3, line 7, "VII" should read --VIII--.

Col. 4, line 12, "hours" should read --hour--.

Col. 5, line 50, "4p-" should read --4-p- --.

Col. 6, line 2, "3a4" should read --3a,4--.

Signed and Sealed this

Seventh Day of September 1976

[SEAL]

Attest:

RUTH C. MASON
Attesting Officer

C. MARSHALL DANN
Commissioner of Patents and Trademarks